United States Patent [19]

Shodeen et al.

[11] Patent Number: 5,446,289
[45] Date of Patent: Aug. 29, 1995

[54] ULTRAVIOLET PASSTHROUGH STERILIZATION DEVICE

[75] Inventors: Keith Shodeen, Otsego, Minn.; Stewart Davenport, Portage, Mich.; Hans L. Melgaard, North Oaks, Minn.

[73] Assignee: Despatch Industries Limited Partnership, Minneapolis, Minn.

[21] Appl. No.: 227,959

[22] Filed: Apr. 15, 1994

[51] Int. Cl.⁶ .............................................. H01J 37/20
[52] U.S. Cl. ........................ 250/455.11; 250/454.11; 250/453.11; 422/24
[58] Field of Search ....................... 250/455.11, 454.11, 250/453.11; 422/24, 25

[56] References Cited

U.S. PATENT DOCUMENTS 2,822,476  2/1958  Osgood .......................... 250/455.11

OTHER PUBLICATIONS

"Product Specification Bulletin for Solarbrite Reflectors," Fuller Ultraviolet Corp., Frankfort, Ill., three pages. No date available.
Brochure entitled "GE Quartz: Fused Quartz Products," pp. 3, 4, 7, 12, 20, and 21. No date available.
Brochure entitled "Infrared Sand Reclamation," BGK Environmental Group, two pages, 1992.
Reich, Robert R., et al, "Laboratory Applications of Ultraviolet Irradiation," MD&DI, Aug. 1985, pp. 52–58.
Whitby, Dr. G. Elliot, and Palmateer, Garry, "Disinfection of Wastewater with Ultraviolet Light," pp. 157–168. No date available.
Janoschek, Robert, and du Moulin, Gary C., "Ultraviolet Disinfection in Biotechnology: Myth vs. Practice" BioPharm, Jan.-Feb. 1994, pp. 24–31.
Taylor, A. H.; "Reflection-Factors of Various Materials for Visible and Ultraviolet Radiation," J. Opt. Soc. Am., Jul. 1934, vol. 24, pp. 192–193.

Primary Examiner—Paul M. Dzierzynski
Assistant Examiner—Kiet T. Nguyen
Attorney, Agent, or Firm—Fredrikson & Byron

[57] ABSTRACT

An ultraviolet sterilization and decontamination system which is particularly useful in ultraviolet passthrough applications. The system includes a shell having a reflective inner surface and a barrier positioned within the shell and spaced inwardly of the inner surface of the shell, the barrier being formed of a material which will transmit at least about 70% of the desired wavelength of ultraviolet light. The space between the shell and the barrier defines a lamp cell for holding one or more ultraviolet lamps and the interior of the barrier defines a sterilization cell wherein items can be sterilized or decontaminated. The barrier is supported within the shell by supports and reflective endwalls substantially seal the lamp cell from the sterilization cell, as well as substantially sealing the sterilization cell and lamp cell from communication with the external environment. The system can be placed for use in sterilizing or decontaminating an item being introduced from a non-sterile environment to a substantially sterile, "clean" environment. In such an application, the endwalls should both include doors permitting operator access to the sterilization zone, with one of the doors being accessible from the "clean" environment and the other door should be accessible from the non-sterile environment.

20 Claims, 5 Drawing Sheets

ULTRAVIOLET PASSTHROUGH STERILIZATION DEVICE

FIELD OF THE INVENTION

The present invention relates to sterilizing the exterior of an item using high intensity ultraviolet light.

BACKGROUND OF THE INVENTION

It is well known in the an that most living organisms cannot survive when exposed to certain wavelengths of intense light (e.g., ultraviolet wavelengths of about 250–260 nm) for a period of time. Small living organisms such as microbes generally cannot survive even short periods of intense ultraviolet (UV) irradiation. For this reason, UV light is frequently used for sterilizing or decontaminating equipment and products in both industrial and laboratory settings. For example, pharmaceutical companies often use UV light to sterilize objects before they are brought into a clean room environment where the pharmaceutical products are tested and manufactured.

In one particular use, UV light is used to sterilize or decontaminate items moving from a non-sterile environment, e.g. a normal atmospheric environment, to a "clean", i.e. decontaminated or sterile, environment. In so doing, it is important that the items being transferred not contaminate the clean environment, such as by beating viable organisms or other such contaminants from the non-sterile area into the clean area on the surface of a container holding sterilized products.

In this application, the item being transferred to a clean area is passed through a UV sterilization chamber, referred to as a ultraviolet passthrough, or UVP, sterilizer. Such UVP's generally have a door or the like in a non-sterile environment, a door in the clean environment, and a number of ultraviolet lamps. Only one of the two doors should generally be open at any given time to prevent the free flow of air-borne contaminants into the clean environment. The UV lamps are generally low-pressure mercury vapor lamps, which tend to have optimal emission distributions, with relatively intense emission in the range of about 253.7 nm.

In using such a UVP device to decontaminate, for example, the exterior surface of a container, an outer door in a non-sterile environment is opened and the container is placed inside the ultraviolet sterilizer, e.g. on top of a rigid support. The outer door is closed and the container is irradiated with ultraviolet light of a desired wavelength for a sufficient time to decontaminate the irradiated surface to the desired degree; an exposure time of about 30 seconds to about 3 minutes to radiation of about 2000–6000 microwatts per square centimeter at a wavelength of about 253.7 nm is usually sufficient to substantially sterilize a surface. The inner door, which opens to a sterile or "clean" environment, is opened after the sterilization cycle is finished and the sterilized container is removed through the inner door into the sterile environment.

One problem of current UVP systems is that they frequently do not irradiate the entire surface area of a container or other item in a single sterilizing cycle. Most such systems provide a rigid framework, e.g. a stiff metal mesh or screen, for supporting items to be sterilized within the UVP. Unfortunately, such supports tend to shield certain portions of the container from the ultraviolet light source, limiting effective sterilization of these surfaces.

Another problem presented by current UVP's is that the mercury vapor lamps can break. If such lamps do break, there is a significant risk of mercury contamination of not only the sterilizer, but also both the non-sterile and sterile environments. If mercury does escape, the entire operation of the contaminated clean room must usually be suspended until the mercury contamination is removed and the room can be returned to its "clean" standards. Mercury contamination can be especially troublesome in the pharmaceutical and medical industries because maximum permissible mercury levels in the clean areas are frequently very low. It is rather difficult and very time consuming to completely remove mercury contamination, so a broken mercury vapor lamp can be a rather expensive problem.

SUMMARY OF THE INVENTION

The present invention substantially alleviates the problems of mercury contamination and partial irradiation. In the present invention an external shell having first and second ends extends along a center line. The shell may have an inner reflective surface defining a chamber extending from the first end to the second end. A transmissive barrier may extend along the center line of the shell and may be spaced inwardly of the shell. The transmissive barrier may be made from a material that transmits at least about 70% of the light at a desired operating wavelength; a wavelength on the order of about 253.7 nm, which is generated by mercury vapor lamps, has proven to be quite effective for sterilization. The space between the inner surface of the shell and the outer surface of the transmissive barrier defines a lamp cell and the inner surface of the barrier defines a sterilization cell.

The barrier is supported within the shell by supports, which are optimally positioned within the chamber to avoid shielding any part of a container placed in the sterilization cell from the illumination of the UV lamps. Reflective end walls are desirably positioned at the first and second ends of the shell and barrier. A first reflective end wall sealingly engages the first ends of the shell and barrier, respectively, and a second reflective end wall sealingly engages the second ends of the shell and barrier, respectively. The reflective end walls substantially seal the lamp cell from the sterilization cell and the outside environments. A reflective door may be positioned in one or both of the end walls, the doors being sealingly engageable with an end of the barrier.

DETAILED DESCRIPTION OF THE PREFERRED EMBODIMENTS

Figure 1:
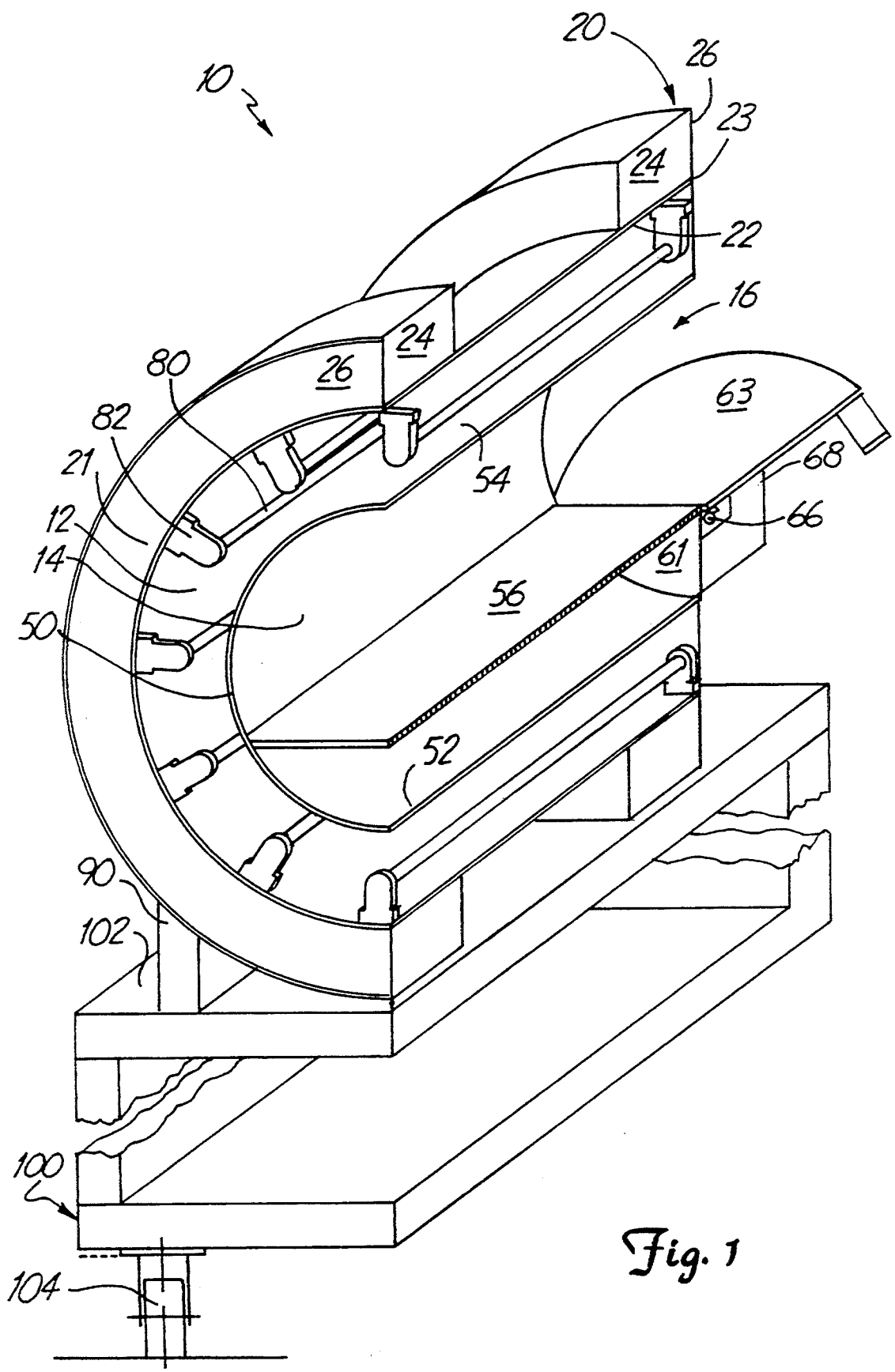
FIG. 1 is a schematic, cross sectional perspective view of an embodiment of the present invention.
Figure 2:
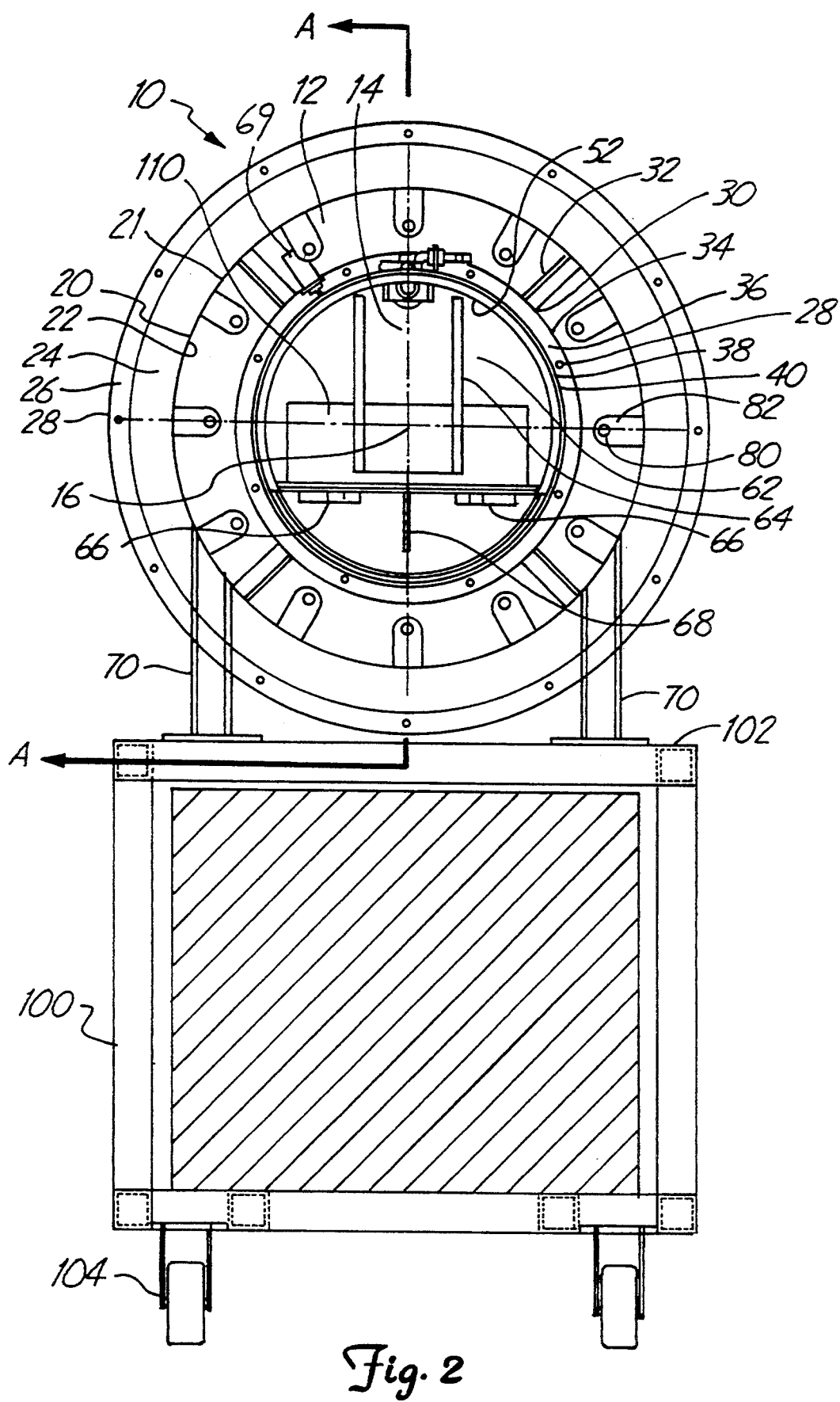
FIG. 2 is a front view of an ultraviolet passthrough sterilizer in accordance with the invention.
Figure 3:
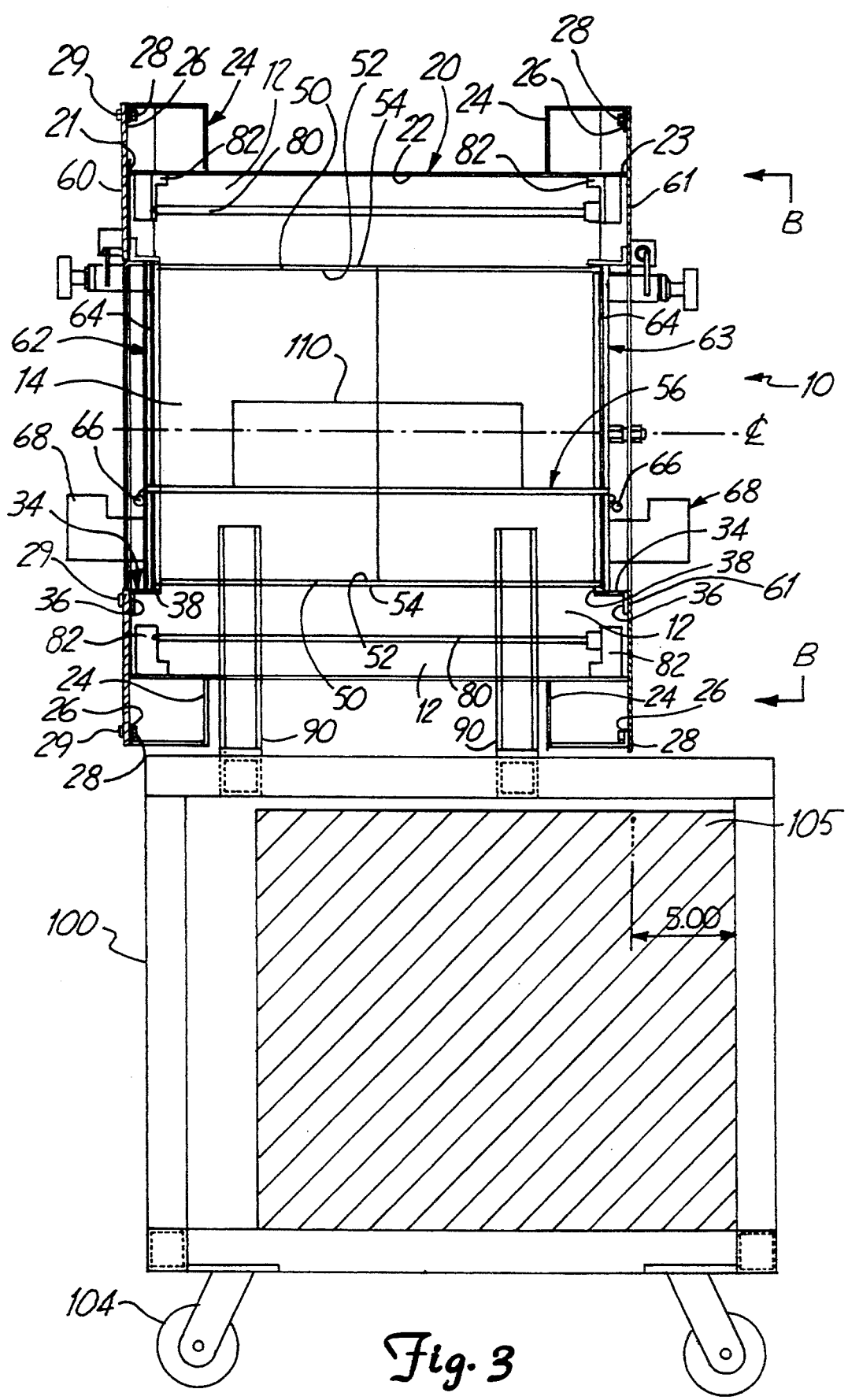
FIG. 3 is a side view of an ultraviolet passthrough sterilizer in accordance with the invention.
Figure 4:
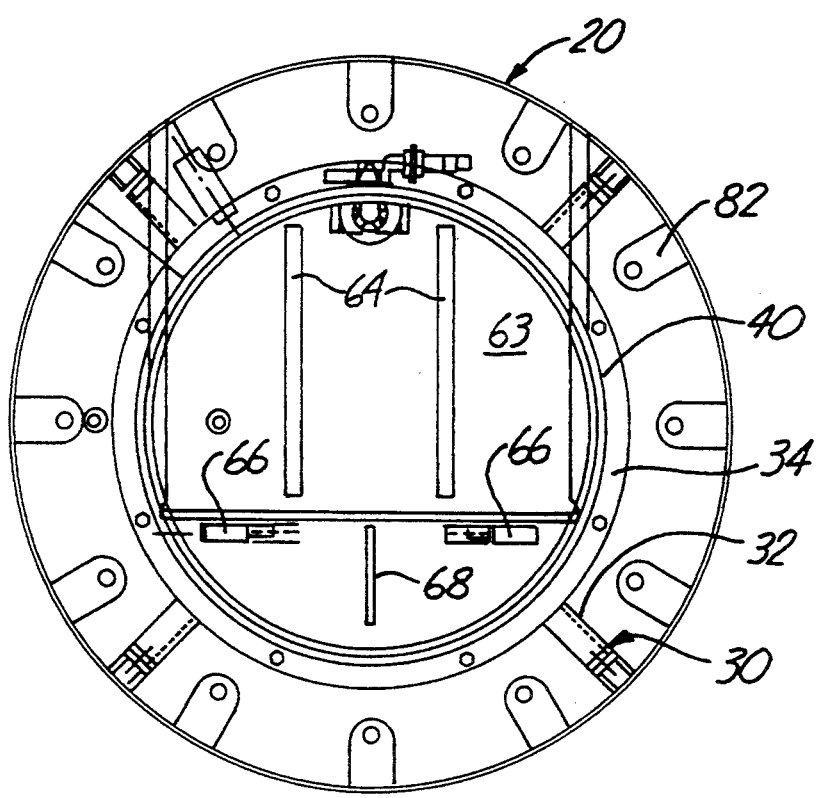
FIG. 4 is a schematic partial rear view of an ultraviolet passthrough sterilizer in accordance with the invention.

FIGS. 1-3 depict an ultraviolet passthrough sterilizer 10 in accordance with the invention. In a preferred embodiment, the sterilizer has a generally cylindrical shell 20 having an inner surface 22 which extends along a center line and terminates in first and second ends 21 and 23, respectively. Although the shape of the shell 20 is shown as being cylindrical, other shapes such as squares, rectangles, or polygons may be used.

In a preferred embodiment, the shell 20 is formed of a durable material which can exhibit acceptable durable in a production environment, such as 316 stainless steel having a #4 finish or other like material. The shell includes an inner surface 22 which defines a chamber 16 extending from the first end 21 to the second end 23. Preferably, the inner surface 22 reflects at least about 80%, and desirably 90% or more, of the light at the required wavelength(s) so that it will serve to redirect any UV light sting the inner wall of the shell back toward the center of the shell.

The inner surface 22 of the wall may be highly polished, or a reflective liner (not shown) may be positioned adjacent to or carded by the inner surface. One particularly effective reflective liner is Solarbrite, manufactured by Fuller Ultraviolet Corp., which can be attached to the inner surface of the shell by means of an adhesive or the like and has a plurality of parabolic indentations that reflect the scattered light towards the center line.

An electrical conduit 24 having a L-shaped cross-section (best seen in FIG. 3) may be attached to the outer surface of the shell 20 some distance away from the first end 21. Another conduit 24 may be similarly attached to the shell 20 some distance away from the second end 23. Since the conduits 24 may be identical as shown in FIGS. 2 and 3, only the conduit associated with the first end will be described. The conduits 24 are adapted to receive wires and the like for supplying power to each of the UV lamps and for completing an electrical connection between each of the lamps, as described below in connection with FIG. 5.

In the embodiment shown in the drawings, one leg of the conduit 24 extends generally radially outwardly from the shell 20, and another leg of the conduit 24 extends generally radially inwardly towards the first end 21. An outer endwall flange 26 may be connected to the conduit 24, and positioned so that the face of the outer endwall flange 26 is flush with the first end 21. The outer end plate flange 26 may alternatively be integral with the conduit 24. A number of holes 27 and nuts 28 may be positioned in the outer endwall flange 26 for receiving a bolts 29 to attach a first endwall 60 (not illustrated in FIG. 1).

Supports 30 may be positioned within the chamber 16 to support a transmissive barrier 50. The supports may be of any suitable size and shape for supporting the barrier within the shell. It is preferred, though, that the supports 30 not interfere with the transmission of illumination from the UV lamps to the sterilization cell, described below. As noted above, this may be accomplished by forming the supports of a material which transmits light of the desired wavelength so that the light can pass through the supports and into the sterilization cell. For example, the barrier 50 and the supports 30 may be formed of the same material and can even be integrally molded of such a material.

In a preferred embodiment illustrated in the present drawings, though, the supports 30 include a number of support posts 32 connected to a support ring 34 (best seen in FIG. 2). The support ring 34 may have an outer support ring flange 36 in which holes 27 and nuts 28 are positioned. The support ring 34 may also have an inner support ring flange 38 which carries a seal 40. In a preferred embodiment, the supports 30 are made from metal and one support is positioned just inside the chamber at each end 21, 23 respectively. The supports may alternatively be made from other materials which transmit the desired wavelength of UV illumination, such as fused silica, and positioned within the chamber 16 at an intermediate point.

A transmissive barrier 50 is positioned within the shell 20 to define a sterilization cell within the shell, with articles to be decontaminated being placed in the sterilization cell. In a preferred embodiment, the barrier 50 is generally cylindrical and has a center line which substantially coincides with the center line of the shell so that the shell and barrier form generally concentric cylinders. It is to be understood that the barrier 50 may have other shapes such as squares, rectangles or other polygons. The barrier 50 and shell 20 may have the same general shape as with concentric cylinders, or the barrier and shell may have different shapes. Having generally concentric cylinders, though, tends to ensure a relatively uniform illumination within the sterilization cell 14, though, as explained below.

In a preferred environment, the barrier 50 transmits at least about 70%, desirably about 75% or more, and optimally about 80% or more, of the desired wavelength(s) of light. It has been found that for most applications a wavelength of about 253.7 nm is particularly effective for sterilization and decontamination. Fused silica has excellent transmission properties for these wavelengths of light and the barrier may be formed of such a material. In one embodiment which has been found to work well, the barrier 50 is about 0.2 inches thick and made from GE 214LD fused quartz, commercially available from General Electric Co., which has a transmissivity of approximately 80% at 253.7 nm.

The barrier 50 is positioned inwardly from the shell 20 so that the space between the outer surface 54 of the barrier 50 and the inner surface 22 of the shell 20 defines a sealable lamp cell 12. Lamp receptacles 82 may be attached to the inner surface 22 of the shell 20 for receiving mercury vapor lamps 80 or other suitable sources of the desired wavelengths of light. In a preferred embodiment, the lamps 80 have an intensity of about 2,000 mW/cm$^2$ at six inches, and emit about 90% of their energy at approximately 253.7 nm. The lamps may be equally spaced around the inner surface 22 of the shell 20, and longitudinally extend along the length of shell.

The lamps 80 should be spaced within the lamp cell 12 to ensure relatively uniform irradiation of the sterilization cell 14. By utilizing generally concentric, cylindrical shells 20 and barriers 50, a relatively uniform illumination of the sterilization cell 14 can be achieved by simply spacing the lamps generally equiangularly about the annular lamp cell defined therebetween. In one preferred configuration, twelve lamps 80 are spaced at about 30° intervals around the inner surface of the shell.

The barrier 50 has an inner surface 52 which defines a sterilization cell 14. The size and shape of the barrier should be selected to provide a sterilization cell which is suitably sized for receiving the items to be decontaminated or sterilized in the UVP system 10 of the invention. If the barrier is generally square in cross section (rather than generally circular, as shown), the barrier will present a horizontal surface which may be suitable for supporting the items to be sterilized. In selecting the configuration of the barrier, the items to be sterilized should be readily positionable at the location within the sterilization cell having the maximum illumination.

If a generally cylindrical configuration, such as shown in FIGS. 1–4, is employed, the most uniform illumination of all sides of the items within the sterilization cell, and hence the efficiency of the sterilization of the overall surface of the items, generally takes place at the center line of the cylinder due to the reflection of UV light by the reflective inner surface of the shell's walls. If a cylindrical barrier 50 is used, a fused silica shelf 56 may be positioned within the sterilization chamber 14 for supporting a container (110 in FIG. 3) or the like for sterilization generally along the centerline of the sterilization cell 14.

The shelf 56 may be generally planar and rectangular in shape, horizontally extending substantially the entire length of the sterilization cavity 14, being supported only at its ends. In a preferred embodiment, the shelf 56 transmits at least about 70%, and desirably at least about 75%, of light in the desired wavelength(s), e.g. approximately 253.7 nm. In one embodiment, the shelf is about ¼ inch thick and made from GE 124 fused quartz, which is also commercially available from the General Electric Company.

Thus, both the barrier 50 and the shelf 56 are formed of transmissive materials, such as fused quartz or the like. Since only materials having high transmissivity values are between the lamps 80 and the container 110, the container is not shielded from a substantial percentage of the ultraviolet light. As such, the present invention radiates the full body of a container in one sterilization cycle without moving the container.

A first endwall 60 (omitted in FIG. 1 for purposes of illustration of the interior of the shell) may be sealingly attached to the outer endwall flange 26 and the outer support ring flange 36 of the first end by threadably engaging bolts 29 with nuts 28. The second endwall 61 may be sealingly attached to the outer endwall flange 26 and outer flange 36 of the second end of the ultraviolet passthrough sterilizer 10 in a similar manner.

The seal between the endwall and the endwall flange and outer support ring flange should be generally airtight to ensure that the various cells of the UVP system are generally sealed from one another. It will be appreciated then that any type of substantially air tight seal such as a gasket or o-ring of suitable material may be used to seal the flanges 26 and 32 to an endwall. The endwalls 60 and 61 seal the lamp cell 12 from the sterilization cell 14 and the outer environments, and the lamp cell thereby defines a generally sealed space. This sealed space will tend to contain any mercury or mercury vapor that is released when one of the lamps breaks. Also, the endwalls 60 and 61 may be removed, providing easy access to the lamps for maintenance.

The sterilization cell 14 may itself be sealed from the outer environments by first and second doors 62, 63 respectively. Since the first and second doors may be identical, only the first door 62 will be described. The first door 62 may be connected at its bottom to the first end of the ultraviolet sterilizer by hinges 66 so that the door will open downwardly and rest on a door support 68. The interior surfaces of the doors are desirably reflective, and a number of low-friction runners 64 may be attached to the interior surfaces to prevent scratching thereof. For example, the inner surface of the door 62 may be made from, 316 stainless steel with a number 7 electropolished finish or a polished aluminum and the runners 64 may be formed of polytetrafluoroethylene, nylon or the like.

When the door is open, the surface of the runners 64 may be in substantially the same plane as the surface of shelf 56. This will enable items to be placed on the door and simply be slid onto the shelf for sterilization or decontamination. The door 62 may be shaped so that it engages the seal 40 on the inner support ring flange 38 when it is closes, thereby sealing the first end of the sterilization chamber 14.

In the embodiment illustrated, there are two doors 62, 63, with one door being positioned at each end of the UVP system 10. As described below, it is preferred that one end of the system be positioned in a non-sterile environment and the other end be positioned in a relatively "clean", sterile environment. By positioning one door at each end, an operator in the dirty environment can open the sterilizer and place an item in the sterilization cell 14. The door can then be closed and the UV lamps can be activated to decontaminate or sterilize the outer surface of the item. An operator can then open the opposite door, positioned in the clean environment, to remove the item from the UVP system for use in the clean environment.

In an alternative embodiment of the present invention, a door 62 is positioned in only one end of the sterilizer 10 rather than having a door at both ends. This embodiment may be used in circumstances where there is not a separate clean environment and dirty environment, but it is necessary to decontaminate or sterilize an item for use. For example, a one-door system can be useful in operating rooms for sterilizing medical devices and the like prior to use.

FIGS. 1–3 illustrate a particularly preferred embodiment of the invention, wherein the UVP unit 10 of the invention is mounted on a transportable support 100. In the embodiment illustrated in the drawings, the transportable support 100 may take the form of a conventional cart, having an upper surface 102 spaced above the floor and a plurality of wheels 104 to enable an operator to move the UVP system. The shell 20 may be attached to the upper surface 102 of the transportable support 100 by means of a pair of support struts 90 or the like to keep the shell stably positioned on the support. Although it may not be necessary to move the UVP system frequently during normal operation, providing the UVP system with a transportable support will enable the UVP system 10 of the invention to be moved out of the way during, for example, renovation of the clean room.

Figure 5:
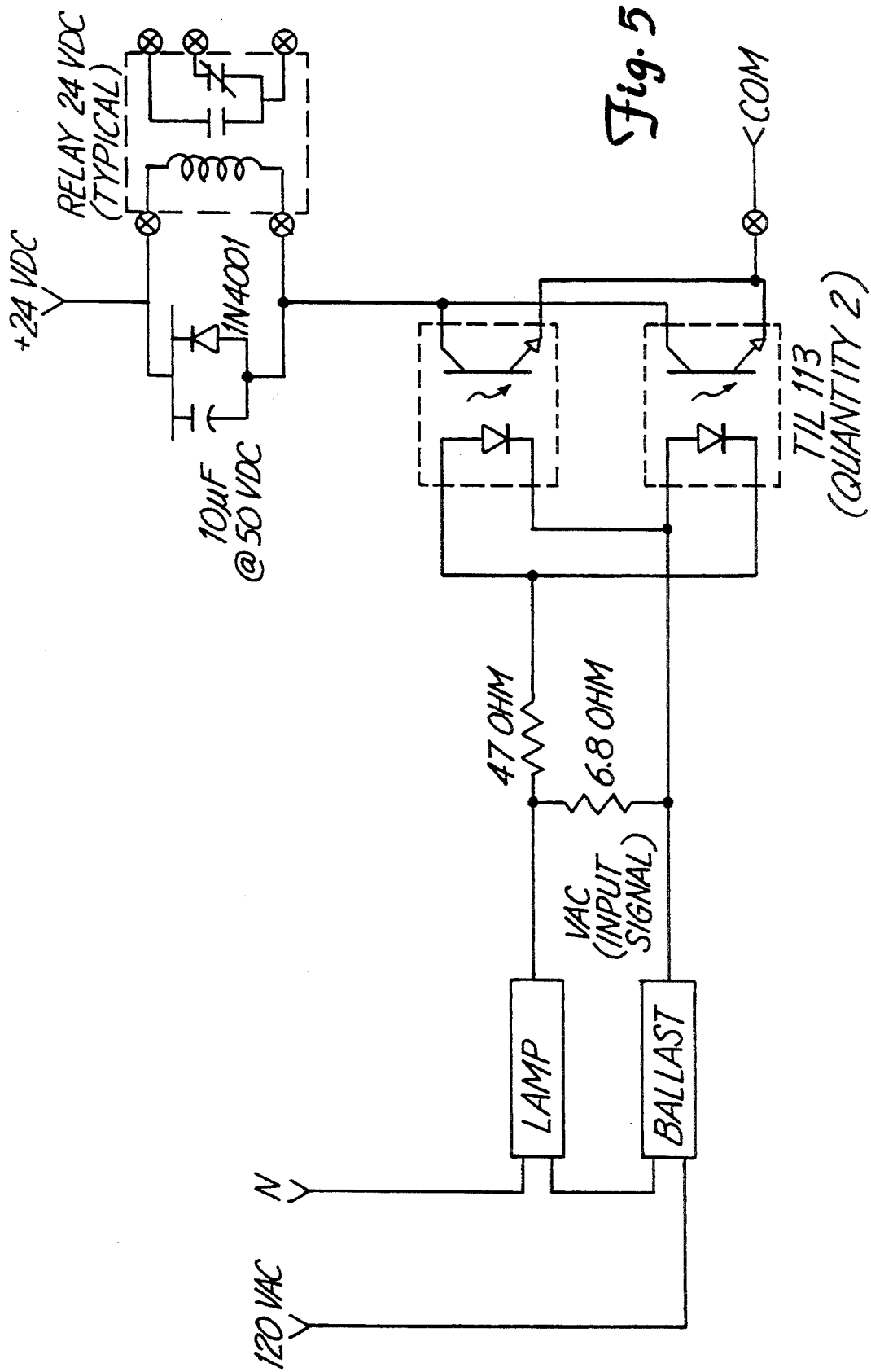
FIG. 5 is a schematic diagram of an electric circuit for automatically verifying the continuing operation of a lamp of the invention.

In a further preferred embodiment, the operational status of individual ultraviolet lamps 80 may be verified without removing the lamps from the sterilizer 10. FIG. 5 depicts a circuit for automatically verifying that each of the lamps is continuing to operate. Lights (not shown) may be installed in a control panel 105 to visually indicate to an operator when a particular lamp 80 is not operating properly, e.g. if the lamp is not emitting energy. In a preferred embodiment, an alarm is activated when an ultraviolet lamp is not emitting energy, and the alarm can only be deactivated by shutting down the sterilizer.

In the embodiment of FIG. 5, a sensor is provided for detecting when the current being drawn by the lamp falls below a predetermined operational threshold. When this sensor relay is open, it will send a signal to a control panel to indicate that the lamp is operational, such as by lighting an LED light on the control panel. If the current passing through the sensor falls below a threshold level, e.g. about 30% of optimal operational power, the relay will instead send a signal to the control panel that the lamp is not operating properly, such as by activating an audible alarm.

The circuit illustrated in FIG. 5 is intended to detect a malfunction in one bulb. It is to be understood that one such circuit may be provided for each bulb and these circuits may be connected to the control panel. In this manner, each independent circuit can send a signal relating to a particular bulb, enabling this fault detection system to not only indicate that one of the lamps may not be operating properly, but also identifying which lamp may be malfunctioning to simplify repair of the system.

An ultraviolet passthrough sterilizer of the present invention may be operated on a typical 115 volt AC outlet. A master power switch (not shown) energizes a control panel (not shown), and in a preferred embodiment, the first door 62 facing the sterile environment is automatically locked and the second door 63 facing the non-sterile environment remains unlocked. A safety system may be included which prevents either both doors from being opened at the same time, or any door from being opened during a sterilization cycle. Such a safety system may also shut the lamps 80 off when any door is opened during the sterilization cycle.

FIG. 5 illustrates an electrical schematic diagram of one preferred embodiment of a system for verifying the operability of one of the lamps in the oven. Other features and aspects of this circuit will be readily seen by those of in the art. In light of the present disclosure, other circuits for performing substantially the same function as that performed by the circuit of FIG. 5 can be readily designed by those of ordinary skill in the art.

After the sterilizer is activated, the second door 63 may be opened and the container 110 inserted into the sterilization cavity 14. The second door 63 is then closed, and the sterilization cycle is activated. In a preferred embodiment, a "cycle on" indicator (not shown) is illuminated, and the second door 63 automatically locks. After the sterilization cycle is complete, a visual indicator (not shown) is activated and remains lit until the inner door is opened. In a preferred embodiment, the first door 62 automatically unlocks after the sterilization cycle is complete.

While a preferred embodiment of the invention has been described, it should be understood that various changes, adaptations and modifications may be made therein without departing from the spirit of the invention and the scope of the appended claims.

What is claimed is:

1. An ultraviolet sterilization device comprising:
   an external shell extending along a center line and having at first and second ends, the shell having an inner surface defining a chamber extending from the first end to the second end;
   a transmissive barrier extending along the center line of the shell and having first and second ends, the barrier being spaced inwardly of the shell to define a lamp cell therebetween, the inner surface of the barrier defining a sterilization cell, the barrier being formed of a material which transmits at least about 70% of light having a wavelength of about 253.7 nm;
   supports adapted for positioning the barrier within the shell;
   a lamp contained within the lamp cell; and
   reflective endwalls including a first reflective endwall sealingly engaging the first ends of the shell and barrier respectively and a second reflective endwall sealingly engaging the second ends of the shell and barrier respectively, the reflective endwalls substantially sealing the lamp cell from the sterilization cell and an outside environment.

2. The ultraviolet sterilization device of claim 1, wherein at least one endwall includes a reflective door, the door having an open position wherein an operator may access the sterilization cell and a closed position wherein it substantially seals the sterilization cell from an outside environment.

3. The ultraviolet sterilization device of claim 2, wherein the endwalls each include a reflective door, a first door sealingly engaging the first end of the barrier and a second door sealingly engaging the second end of the barrier, one of the doors being accessible from a non-sterile environment and the other of the doors being accessible from a substantially sterile environment.

4. The ultraviolet sterilization device of claim 3 further comprising a fused silica shelf positioned within and extending substantially throughout the length of the sterilization cell, the doors being positioned so that each inner surface of the doors lies in substantially the same plane as the shelf when the doors are opened.

5. The ultraviolet sterilization device of claim 1, wherein the shell is generally cylindrical in shape.

6. The ultraviolet sterilization device of claim 5, wherein both the shell and the barrier are generally cylindrical in shape and have center lines, the center line of the shell substantially coinciding with the center line of the barrier so that the shell and the barrier together define generally concentric cylinders.

7. The ultraviolet sterilization device of claim 5 further comprising a plurality of lamps sources spaced generally equiangularly about the generally cylindrical inner surface of the shell.

8. The ultraviolet sterilization device of claim 1, wherein the barrier is generally cylindrical in shape and is formed of a fused silica.

9. The ultraviolet sterilization device of claim 1 further comprising a plurality of lamps equally spaced circumferentially around the inner surface of the shell.

10. The ultraviolet sterilization device of claim 9 further comprising means for remotely verifying the operability of a lamp without visually inspecting the lamp.

11. The ultraviolet sterilization device of claim 10 further comprising an alarm indicating a failure of a lamp.

12. The ultraviolet sterilization device of claim 1 further comprising a transmissive shelf positioned within and extending substantially throughout the length of the sterilization cell.

13. The ultraviolet sterilization device of claim 12, wherein the shelf is formed of fused silica.

14. The ultraviolet sterilization device of claim 1, wherein the transmissive barrier is formed of fused silica and transmits at least about 80% of light having a wavelength of about 253.7 nm.

15. The ultraviolet sterilization device of claim 1 further comprising a reflective liner positioned between the inner surface of the shell and the lamp.

16. The ultraviolet sterilization device of claim 15, wherein the reflective surface is a reflective Solarbrite film.

17. An ultraviolet passthrough sterilization device for passing items from a non-sterile environment to a substantially sterile environment comprising:

a generally cylindrical external shell extending along a center line and having a first end accessible from the non-sterile environment and a second end accessible from the substantially sterile environment, the shell having a reflective inner surface which defines a chamber extending from the first end to the second end;

a generally cylindrical fused quartz barrier extending along the center line of the shell and having a first end accessible from the non-sterile environment and a second end accessible from the substantially sterile environment, the barrier being positioned generally concentrically within the shell and spaced radially inwardly of the inner surface of the shell to define a lamp cell therebetween, an inner surface of the barrier defining a generally cylindrical sterilization cell;

supports adapted for positioning the barrier within the shell;

a plurality of lamps spaced generally equiangularly about the inner surface of the shell and contained within the lamp cell;

a fused quartz shelf positioned horizontally within and extending along substantially the entire length of the sterilization cell;

reflective endwalls having openings for receiving reflective doors and including a first reflective endwall sealingly engaging the first ends of the shell and barrier respectively and a second reflective endwall sealingly engaging the second ends of the shell and barrier respectively, whereby the first and second endwalls substantially seal the lamp cell from the sterilization cell, the sterile environment, and the non-sterile environment; and the reflective doors including a first door positioned in the opening through the first endwall and sealingly engaging the first end of the barrier, and a second door positioned in the opening through the second endwall and sealingly engaging the second end of the barrier.

18. The ultraviolet sterilization device of claim 12, wherein the reflective inner surface is Solarbrite.

19. The ultraviolet sterilization device of claim 12 further comprising a means for verifying the intensity of the lamps without removal thereof.

20. The ultraviolet sterilization device of claim 12 wherein the barrier is adapted to transmit at least about 70% of light having a wavelength of about 253.7 nm.

* * * * *